United States Patent [19]

Ferrante et al.

[11] Patent Number: 5,275,603
[45] Date of Patent: Jan. 4, 1994

[54] ROTATIONALLY AND ANGULARLY ADJUSTABLE TIBIAL CUTTING GUIDE AND METHOD OF USE

[75] Inventors: Joseph M. Ferrante; Alfred J. Fichera, both of Cordova, Tenn.; Leo A. Whiteside, Chesterfield, Mo.

[73] Assignee: Wright Medical Technology, Inc., Arlington, Tenn.

[21] Appl. No.: 838,093

[22] Filed: Feb. 20, 1992

[51] Int. Cl.$^5$ ............................................. A61F 5/00
[52] U.S. Cl. ........................................ 606/86; 606/87
[58] Field of Search ............... 606/79, 62, 53, 57, 606/78, 82, 88, 96, 86, 87; 623/16, 17

[56] References Cited

U.S. PATENT DOCUMENTS

| | | | |
|---|---|---|---|
| 4,467,801 | 8/1984 | Whiteside | 128/303 R |
| 4,474,177 | 10/1984 | Whiteside | 606/62 |
| 4,487,203 | 12/1984 | Androphy | 606/62 |
| 4,703,751 | 11/1987 | Pohl | 606/62 |
| 4,721,104 | 1/1988 | Kaufman | 606/88 |
| 4,736,737 | 4/1988 | Fargie | 606/88 |
| 4,773,407 | 9/1988 | Petersen | 606/88 |
| 4,791,919 | 12/1988 | Elloy | 606/62 |
| 4,952,213 | 8/1990 | Bowman | 606/62 |
| 5,049,149 | 9/1991 | Schmidt | 606/88 |
| 5,053,039 | 10/1991 | Hofmann | 606/86 |
| 5,108,396 | 4/1992 | Lackey | 606/62 |

*Primary Examiner*—Michael A. Brown

[57] ABSTRACT

The present invention provides a cutting guide for ostectomy of the medial and lateral tibial surface during knee surgery. The cutting guide comprises a guide block including an axial opening defined along the longitudinal axis of the tibial canal. The guide block being adapted for attachment to a tibial trial base including alignment holes for locating the proper degree of rotational alignment of the tibial trial base with respect to the longitudinal axis of the tibia to assure the proper varus-valgus orientation and anterior-posterior slope of the resected tibial surface with respect to the femur. A pair of blade slots are provided for guiding a cutting tool for making a wedge-shaped resection of the tibia to accommodate a tibial tray component having a preselected internal distal surface corresponding to that of the resected tibia. The blade slots are pivotally mounted for selectively adjusting the angular alignment of the blade slots with respect to the lateral-medial axis perpendicular to the longitudinal axis of the tibia.

10 Claims, 4 Drawing Sheets

ROTATIONALLY AND ANGULARLY ADJUSTABLE TIBIAL CUTTING GUIDE AND METHOD OF USE

TECHNICAL FIELD

This invention relates to a method and instrumentation for shaping the proximal surface of the tibia. More particularly, an adjustable cutting guide for preparing a proximal tibial surface to receive a prosthesis component.

BACKGROUND OF THE INVENTION

In replacing a knee joint which has been damaged due to disease or trauma, it is important that the prosthesis used to replace the damaged portion of the joint be properly aligned with respect to the bone to which the prosthesis is fixed. If the tibial surface does not lie in the correct plane, the implanted prosthesis may not properly articulate with the distal femoral prosthesis when the knee joint is reduced, and complications can result. Particular problems are encountered when resection of either the medial or lateral tibial surface is required, in that available shaping instruments require sacrificing the entire proximal surface. Rather, the stability of the prosthesis and knee is significantly improved by retaining as much of the proximal surface as possible.

DESCRIPTION OF THE PRIOR ART

A conventional tibial cutting guide is generally used to resect the proximal tibial surface transversely with respect to the central long axis of the tibia. An example of such a cutting guide can be found in U.S. Pat. No. 4,952,213 to Bowman, et al., which discloses using an intramedullary rod placed into the medullary canal to establish a first axis. A rotatable bar extends perpendicularly from and is affixed to the intramedullary rod and is connected to a pivot device, which in turn is connected to a support arm that holds a saw guide against a proximal portion of the tibia bone. The rotation angle of the intramedullary rod determines the medial-lateral inclination of the saw guide and the pivot device determines the anterior-posterior inclination of the saw guide. The rotatable bar is slideable axially along the intramedullary rod to adjust the cut depth of the saw guide. With the saw guide properly positioned in the desired angular orientation, the saw guide is rigidly attached to the tibia bone using retaining pins and the remainder of the apparatus removed. A saw is then inserted in the saw guide and the entire proximal surface resected.

Such conventional tibial cutting guides as described above are limited in that the entire proximal tibial surface is resected and thus sacrificed to remove a deformity in the medial or lateral tibial surface. Moreover, removing excess bone can cause the prosthesis to become unstable, resulting in additional revision surgeries.

The present invention provides instrumentation for resecting a portion of the proximal tibial surface during knee surgery. The instrument comprises a trial base and a guide block having an anterior surface, and opposed proximal and distal surfaces, the guide block being adapted for attachment to the base. Means are provided for rotationally aligning the trial base for proper coverage and with respect to the femoral component. Means are further provided for guiding a cutting tool to make a wedge-shaped resection of the tibia to accommodate a tibial tray component having a preselected internal distal surface corresponding to that of the resected tibia, the guide means being rotatable about a lateral-medial axis, including means for selectively adjusting the rotational alignment of the guide means about the lateral-medial axis perpendicular to the longitudinal axis of the tibia. Means are also included for connecting the instrument to the tibial trial base.

There appears to be a need for a method and tibial cutting guide enabling a surgeon to isolate a deformity in either the medial or lateral tibial surface and perform a resection while sparing that portion of the proximal tibial surface which is healthy.

An advantage of the present invention is to provide a tibial cutting guide that requires fewer alignment steps, while allowing greater accuracy in resecting the proximal tibia relative to the central long axis of the tibia.

Another advantage of the present invention is a tibial cutting guide that utilizes a tibial trial base to define a reference plane for accurately determining the proper orientation for rotation and coverage of the tibial implant with respect to the longitudinal axis of the tibia.

BRIEF DESCRIPTION OF THE DRAWINGS

The invention may be better appreciated by reference to the attached Drawings, which illustrate one or more preferred embodiments, wherein.

DETAILED DESCRIPTION

Figure 1:
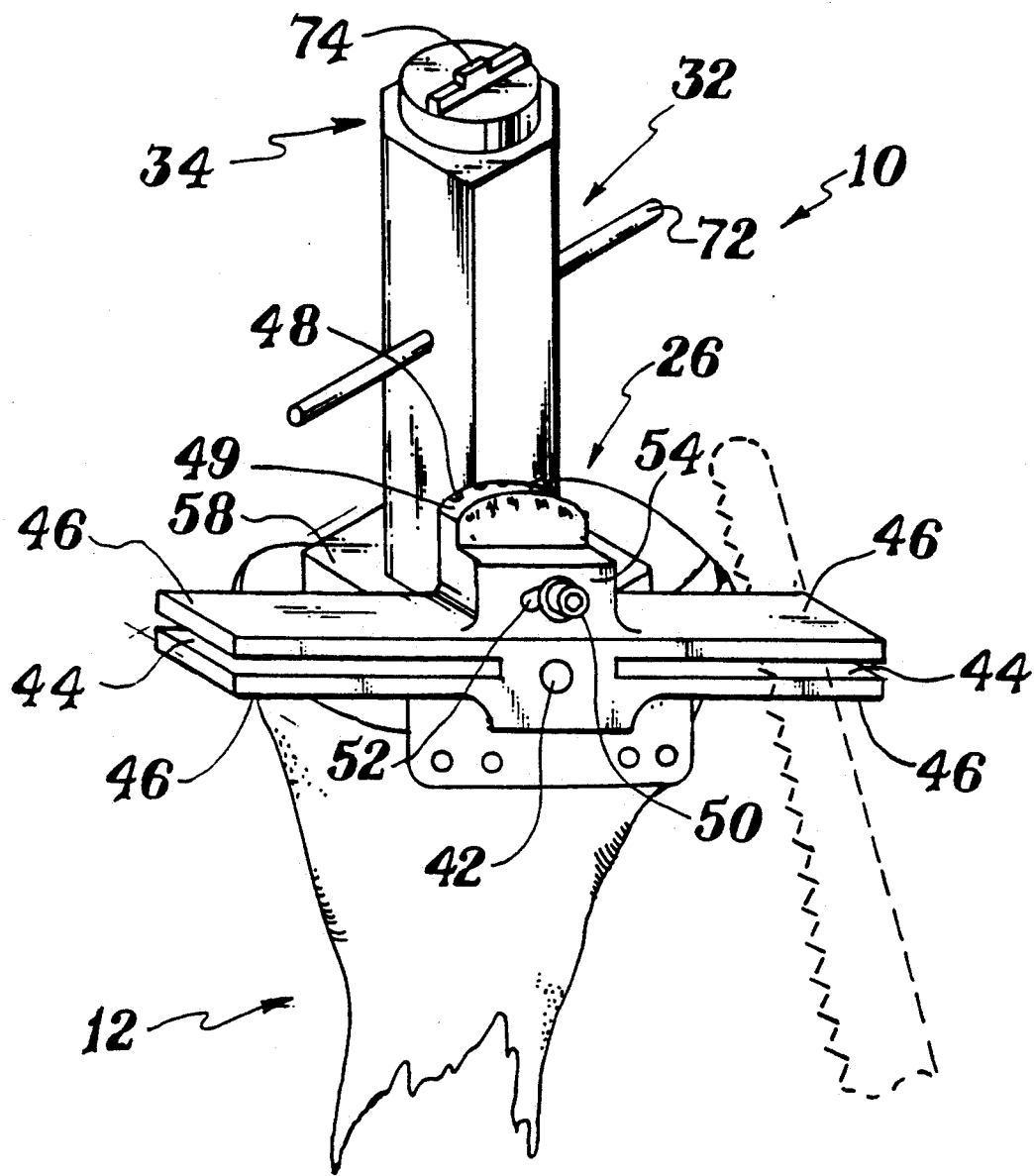
FIG. 1 is a perspective view of the tibial cutting guide according to the present invention in an operative position on a human tibia.
Figure 2:
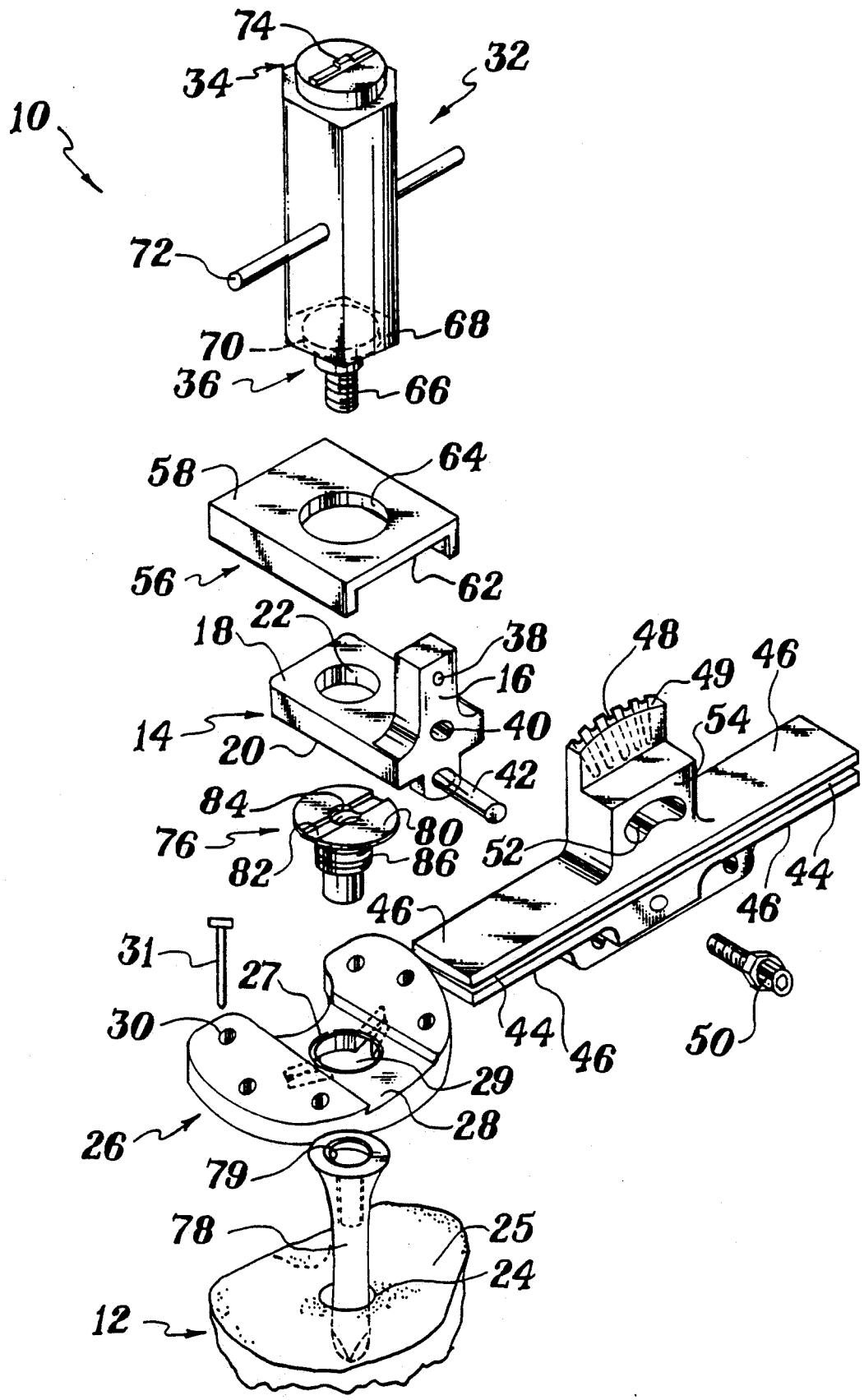
FIG. 2 is an exploded perspective view of the tibial cutting guide.

Referring to FIGS. 1 and 2, a preferred embodiment of instrumentation for ostectomy of the proximal tibial surface is generally shown at 10, in a representative position on tibia 12. It will be understood that, in the case shown, the tibial 12 has been already resected such that a portion of the proximal surface of tibia bone 12 will be presently removed to shape the tibial surface for later implantation; discussed below. As shown in FIG. 2, the instrument 10 comprises a guide block 14 having an anterior surface 16, and opposed proximal 18 and distal 20 surfaces including an axial opening 22 defined along the longitudinal axis of the tibia 12. The guide block 14 is adapted for attachment to a tibial trial base, generally indicated at 26 including axial aperture 29. Means more specifically detailed herein are provided for locating the proper degree of rotational alignment of trial base 26 with respect to the longitudinal axis 24 of tibia 12 to assure the proper tibial coverage and orientation with the femoral part of the prosthesis. Means are further provided for guiding a cutting tool for making a wedge-shaped resection of tibia 12 to accommodate a tibial tray component having a preselected internal distal surface corresponding to that of the resected tibia as will be appreciated below, preferably, the guide means is pivotally mounted to the anterior surface 16 of the guide block 14, while additional means are provided for selectively adjusting the rotational alignment of the guide means with respect to the lateral-medial axis perpendicular to the longitudinal axis of tibia 12. Means are further included for interlocking the instrument 10 to tibial trial base 26.

Referring further to FIG. 2, the guide block 14 has an anterior surface 16 and opposed proximal 18 and distal 20 surfaces including an axial opening 22 defined along the longitudinal axis 24 of the tibia 12. Opening 22 serves as a passageway for interlocking guide block 14 to tibial trial base 26. It will be understood by those skilled in the art that axial opening 22 can be used as a reference for generally locating instrument 10 with respect to the longitudinal axis of tibia 12, however, the guide means is located with reference to the trial base, as will be appreciated by those skilled in the art. Anterior surface 16 further includes ball plunger assembly 38, screw hole 40, and axially-extending post 42, for pivotally mounting the guide means.

FIG. 2 also shows tibial trial base 26 having a plurality of aligning holes 30, femoral runner 28 and axial aperture 29. Alignment pin 31 is inserted through aligning holes 30 and into surface 25 of tibia 12. Femoral runner 28 is slightly wider than guide block 14, allowing the guide block to be seated within the runner such that aperture 29 is aligned with opening 22. Tibial trial stem 78 having internal threads 79 is adapted for attachment to tibial trial base 26, for anchoring the trial base in the medullary canal 24 of the tibia.

Figure 3:
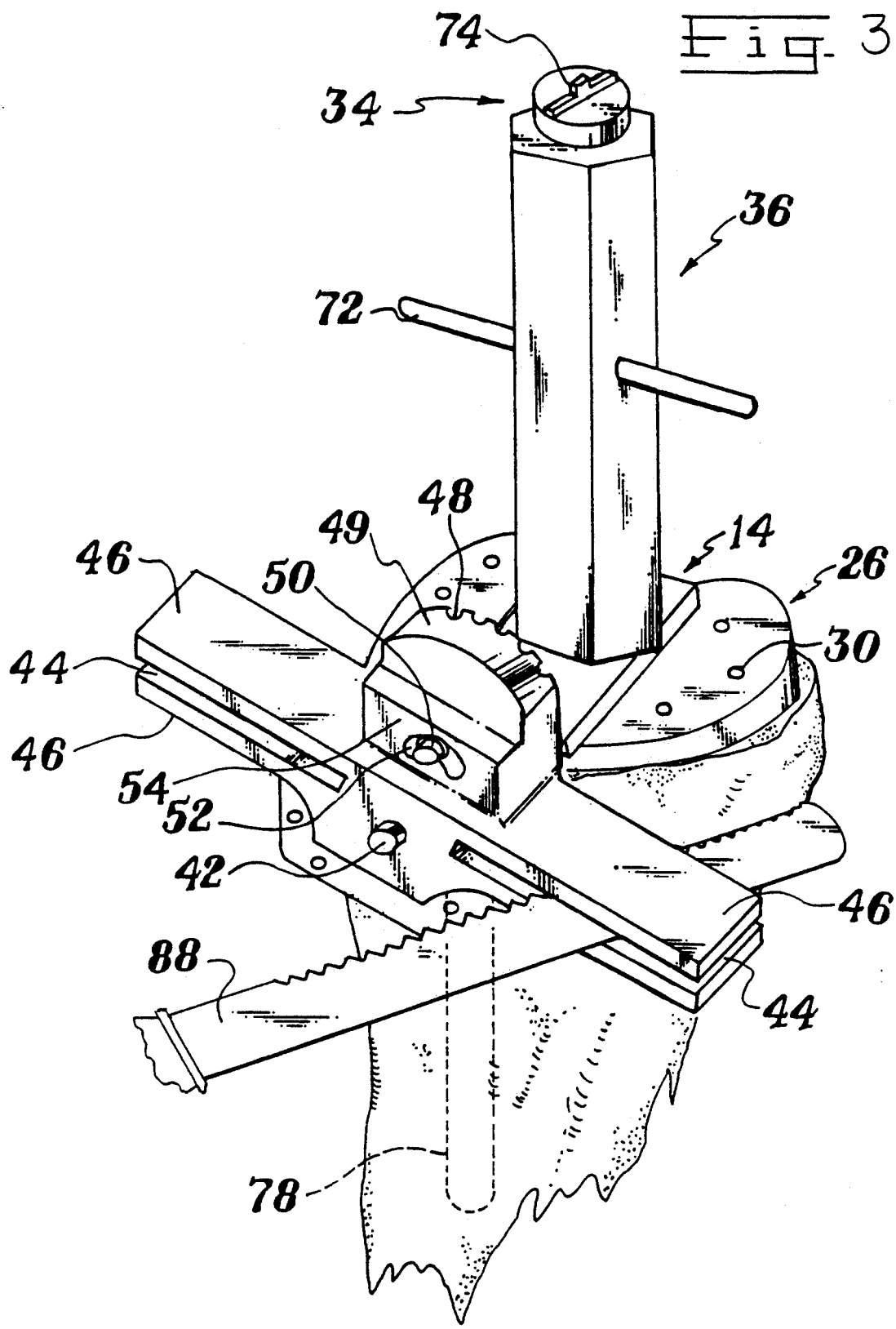
FIG. 3 is a perspective view of the tibial cutting guide and a cutting tool according to the present invention shown in an operative position for resecting a human tibia.

As shown in FIGS. 1, 2, and 3 the guide means is pivotally mounted on post 42 extending from anterior surface 16 of guide block 14. The guide means further comprises at least one and preferably a pair of blade slots 44 defined by horizontally-spaced parallel plates 46, so that the guide means can be pivoted on post 42 to resect the medial or lateral surface, or both surfaces of tibia 12 in a single procedure without rotating tibial trial base 26. The instrument can be used for primary tibial resection, but the preferred use is for revision surgery resection. A cutting tool, such as an osteotome 88 shown in FIG. 3, is inserted into blade slot 44 for making a wedge-shaped resection of the proximal tibia to accommodate a preselected tibial prosthesis component.

Referring again to FIG. 2, the adjustment means includes ball plunger assembly 38 extending from anterior surface 16 of guide block 14 mating with indents 48 formed in flange 49 of the guide means. As ball plunger assembly 38 engages indents 48, the guide means is releasably locked in one of the five angular positions. Indents 48 act to prevent movement of guide means, unless a certain excess force is applied to overcome the pressure exerted between ball plunger assembly 38 against and indents 48. The angular movement of the guide means varies between 0°0 and 22° taking into account a medial or lateral resection of tibia 12, i.e., the indents 48 represent angles of −22°, −12°, 0, 12°, and 22°, respectively. These angles are selected to correspond to the predetermined angle of a tibial tray component; however, it will be understood that the angles could be arranged to correspond to the angle of the particular tibial tray component being implanted.

As shown in FIG. 2, guideway 52 is formed in the guide means for locking the guide means in the selected angular position. Threaded screw 50 is inserted through guideway 52 and threaded into screw hole 40 formed in anterior surface 16 of guide block 14. Threaded screw 50 engages flattened surface 54 of the guide means to lock the guide mean at the angular position selected. Other adjustable locking means can be substituted by those skilled in the art.

Alternatively, spacer plate, generally shown at 56 is provided with an proximal surface 58 and distal 62 surfaces including an axial passage 64 which aligns with aperture 22 of guide block 14. Spacer plate 56 is adapted to be situated over guide block 14 to accommodate the width of the femoral runner of a medium to extra-large tibial trial base.

As shown in FIG. 2, a handle, generally shown at 32, includes opposed proximal 34 and distal 36 ends, wherein the distal end has threaded portion 66 and the proximal end driver portion 74. The distal 36 end further includes first 68 and second 70 taper. First taper 68 is slightly smaller in diameter than axial opening 22 for insertion through opening 22 of guide block 14. Second taper 70 is slightly smaller in diameter than passage 64 for insertion through the passage of spacer plate 56, as the spacer plate is situated over the guide block when a medium to extra large prosthesis is implanted. A perpendicular cross member 72 is provided through handle 32 to assist the surgeon in rotating the handle when securing and removing it from the cutting guide 10. Handle 32 maintains the guide block 14 and trial base 26 interlocked during the resection procedure.

As shown in FIG. 2, the interlocking means includes trial screw 76, tibial trial stem 78 and handle 34. Specifically, trial screw 76 includes a flatten surface 80 having groove 82, threaded bore 84 and external threads 86. Flattened surface 80 is adapted to seat within counter bore 27, flush within femoral runner 28 as the trial screw 76 is inserted through axial aperture 29. Groove 82 is adapted to receive driven portion 74 of handle 32. Threaded bore 84 engages threaded portion 66 of the handle and external threads 86 engages internal thread 79 of tibial trial stem 78.

The manner in which the method of the present invention may be carried out will now be described. The proximal tibial surface is prepared in the manner described in U.S. Pat. No. 4,467,801 to Leo A Whiteside. The proximal surface of a tibia is prepared to receive a proximal tibial prosthesis by employing a reamer/alignment guide which is used to internally locate the central long axis of the tibia and a plateau planer which cooperatively engages a guide handle attached to the reamer/alignment guide to accomplish the primary shaping of the proximal tibial surface. The reamer/alignment guide has a rod portion extending into the interior of the tibial shaft whose central long axis is aligned with the central long axis of the tibia. The guide handle is concentric with that rod portion such that the plateau planar assumes the proper alignment with respect to the central long axis of the tibia such that the proximal tibial surface is shaped relative to that axis in a simple and accurate manner. The entire disclosure of U.S. Pat. No. 4,467,801, is expressly incorporated by reference herein and relied upon.

Following preparation of the tibia, the appropriate size of tibial trial base 26 is situated on surface 25 of tibia 12 to determine if the surface is sufficiently covered without significant overhang. Trial base 26 is then removed from surface 25 and interlocked to tibial trial stem 78 by inserting driver portion 74 of handle 32 into groove 82 of trial screw 76 and threading the trial screw into threaded bore 79 of the trial stem. With tibial trial stem 78 interlocked to tibial trial base 26, the trial stem is then inserted into tibial canal 24.

Guide block 14 of tibial cutting guide 10 is seated within femoral runner 28 with opening 22 aligned with surface 80 of trial screw 76. In the case where a medium through extra large tibial trial base 26 is used, spacer plate 56 is situated over guide block 14 with passage 64 aligned with axial opening 22. Various widths of spacer plate 56 are used to accommodate the wider femoral runner of medium to extra large tibial trial base 26.

As guide block 14 is situated on tibial trial base 26, first taper 68 is inserted through opening 22. If a medium through extra large tibial trial base is used, second taper 70 is inserted through passage 64 of spacer plate 56. The surgeon holding cross member 72 rotates handle 32, thus threading thread portion 66 into thread bore 84 of trial screw 76, interlocking the handle to guide block 14. Handle 32 remains interlocked to guide block 14 during the resection procedure.

As shown in FIG. 3, the angular alignment of tibial cutting guide 10 is adjusted by pivoting the guide means until ball plunger assembly 38 engages one of the five indents 48. Once the correct angular alignment is selected, threaded screw 50 is tightened against surface 54 to lock the guide means at the desired angle. The guide means can be pivotally adjusted to enable the surgeon to resect a 12°0 or 22° wedge section from the medial or lateral surface of the tibia.

After angular alignment, the proper degree of rotational alignment of tibial trial base 26 about the longitudinal axis of tibia 12 is retained by inserting at least one alignment pin 31 through alignment holes 30 and into surface 25. Alignment pin 31 is inserted opposite the surface to be resected, such that the pin does not interfere with the cutting tool.

Figure 4:
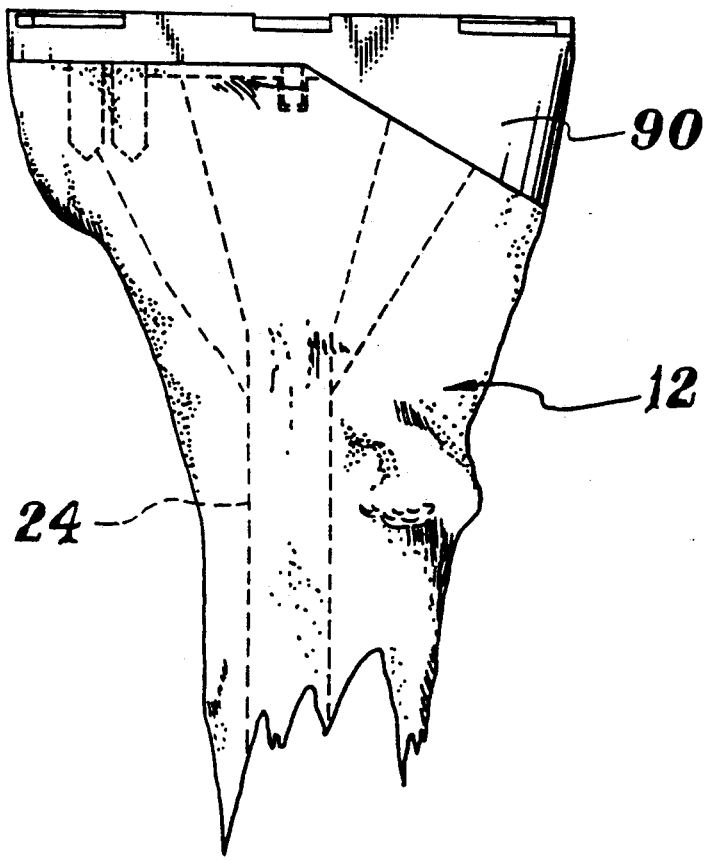
FIG. 4 is a perspective view showing an implanted tibial tray prosthesis.

FIG. 3 shows a cutting tool, such as oscillating saw blade 88, inserted in blade slot 44 for making a wedge-shaped medial resection of tibia 12. Tibial cutting guide 10 including tibial trial stem 78 are removed and replaced with the wedge-shaped tibial component 90 as shown in FIG. 4.

Other modifications of the cutting guide and method of the present invention will become apparent to those skilled in the art from an examination of the above specification and drawings. Therefore, other variations of the present invention may be made which fall within the scope of the following claims even though such variations were not specifically discussed above.

That which is claimed is:

1. A cutting guide for ostectomy of the proximal tibial surface during knee surgery comprising:
   a tibial trial base having a plurality of aligning holes formed therein;
   a guide block having an anterior surface, and opposed proximal and distal surfaces including an axial opening defined along the longitudinal axis of the tibial canal, the guide block being adapted for attachment to said tibial trail base, said tibial trial base having an axial opening
   means for locating the proper degree of rotational alignment of the tibial trial base with respect to the longitudinal axis of the tibia to assure the proper coverage and alignment with the mating femoral component;
   means for guiding a cutting tool for making a wedge-shaped resection of the tibia to accommodate a tibial tray component having a preselected internal distal surface corresponding to that of the resected tibia, the guide means being mounted to the anterior surface of the guide block;
   means for selectively adjusting the angular alignment of the guide means with respect to the lateral-medial axis perpendicular to the longitudinal axis of the tibia;
   means for connecting the guide block to the tibial trail base during resection; and
   a handle having a central axis with opposed proximal and distal ends, the distal end including means for interlocking the guide block to the tibial trial base, the handle remaining fixed to the tibial trial during the resection process, such that the guide means is held in proper alignment with respect to the longitudinal axis without the necessity of intermedullary tibial instrumentation.

2. The cutting guide of claim 1 wherein the guide means comprises at least one blade slot formed by a pair of parallel plates separated by a certain distance.

3. The cutting guide of claim 2 wherein the guide means comprises a pair of blade slots formed by a pair of parallel plates separated by a certain distance, the guide means being pivotally mounted to the anterior surface at the guide block.

4. The cutting guide of claim 1 wherein the interlocking means includes the handle having opposed proximal and distal ends, wherein the distal end of the handle threadly engages a lock screw to secure the cutting guide to the tibial trial base and the handle remains fixed to the cutting guide during resection.

5. The cutting guide of claim 1 further including a spacer plate wherein a spacer plate has opposed proximal and distal surfaces including an axial passage defined along a longitudinal axis of the tibial canal and adapted to be attached to a medium to extra large size tibial trial base for accommodating the width of the femoral runner.

6. The cutting guide of claim 1 wherein a tibial trial stem having internal threads is interlocked to the tibial trial base, and the tibial trial stem anchored within the tibial canal.

7. A cutting guide for ostectomy of the proximal tibial surface during knee surgery comprising:
   a guide block having an anterior surface, and opposed proximal and distal surfaces including an axial opening defined along the longitudinal axis of the tibial canal, the guide block being adapted for attachment to a tibial trial base having an axial aperture;
   means for locating the proper degree of rotational alignment of the tibial trial base with respect to the longitudinal axis of the tibia to assure the proper coverage and alignment with the mating femoral component;
   means for guiding a cutting tool for making a wedge-shaped resection of the tibia to accommodate a tibial tray component having a preselected internal distal surface corresponding to that of the resected tibia, the guide means being mounted to the anterior surface of the guide block;
   a mechanism for selectively adjusting the angular alignment of the guide means with respect to the lateral-medial axis perpendicular to the longitudinal axis of the tibia, the adjustment mechanism including a ball plunger assembly, a plurality of indents, and a threaded screw, the ball plunger assembly being formed in the anterior surface of the guide block and being engagable with the indents formed in the guide means to selectively adjust the angular alignment of the guide means with respect to the lateral-medial axis perpendicular to the longitudinal axis of the tibia, the threaded screw being insertable through a guideway formed in the guide means, the threaded screw being adapted to be threaded into the guide block for tightening against the guide means to lock the guide means in position with respect to the lateral-medial axis perpendicular to the longitudinal axis of the tibia;

means for connecting the guide block to the tibial trial base during resection; and a handle having a central axis with opposed proximal and distal ends, the distal end including means for interlocking the guide block to the tibial trial base, the handle remaining fixed to the tibial trail during the resection process, such that the guide means is held in proper alignment with respect to the longitudinal axis without the necessity of intermedullary tibial instrumentation.

8. The cutting guide of claim 7 wherein the angular alignment of the guide means with respect to the lateral-medial axis perpendicular to the longitudinal axis of the tibia can have an offset of about 0° to 22°.

9. A cutting guide for ostectomy of the proximal tibial surface during knee surgery comprising:

a guide block having an anterior surface, and opposed proximal and distal surfaces including an axial opening defined along the longitudinal axis of the tibial canal, the guide block being adapted for attachment to a tibial trial base having an axial aperture;

a tibial trial stem having internal threads is interlocked to the tibial trail base, and the tibial trial stem anchored within the tibial canal;

means for locating the proper degree of rotational alignment of the tibial trail base with respect to the longitudinal axis of the tibia to assure the proper varus-valgus orientation and anterior-posterior slope of the resected tibial surface with respect to the femur;

a pair of blase slots formed by a pair of parallel plates separated by a certain distance for guiding a cutting tool for making a wedge-shaped resection of the tibia to accommodate a tibial tray component having a preselected internal distal surface corresponding to that of the resected tibia, the blade slots being pivotally mounted to the anterior surface of the guide block;

a ball plunger assembly, a plurality of indents, and a threaded screw, the ball plunger assembly being formed in the anterior surface of the guide block and being engagable with the indents formed in the guide means to selectively adjust the angular alignment of the guide means with respect to the lateral-medial axis perpendicular to the longitudinal axis of the tibia, the threaded screw being insertable through a guideway formed in the guide means, the threaded screw being adapted to be threaded into the guide block for tightening against the guide means to lock the guide means in position with respect to the lateral-medial axis perpendicular to the longitudinal axis of the tibia; and means for interlocking the guide block to the tibial trial base during resection;

a handle having a central axis with opposed proximal and distal ends, the distal end including means for interlocking the guide block to the tibial trail base, the handle remaining fixed to the tibial trail during the resection process.

10. A cutting guide for ostectomy of the proximal tibial surface during knee surgery comprising:

a guide block having an anterior surface, and opposed proximal and distal surfaces including an axial opening defined along the longitudinal axis of the tibial canal, the guide block being adapted for attachment to a tibial trial base having an axial aperture;

a tibial trial stem having internal threads is interlocked to the tibial trail base, and the tibial trial stem anchored within the tibial canal;

means for locating the proper degree of rotational alignment of the tibial trail base with respect to the longitudinal axis of the tibia to assure the proper varus-valgus orientation and anterior-posterior slope of the resected tibial surface with respect to the femur;

a pair of blade slots formed by a pair of parallel plates separated by a certain distance for guiding a cutting tool for making a wedge-shaped resection of the tibia to accommodate a tibial tray component having a preselected internal distal surface corresponding to that of the resected tibia, the blade slots being pivotally mounted to the anterior surface of the guide block;

a spacer plate having opposed proximal and distal surfaces including an axial passage defined along a longitudinal axis of the tibial canal and adapted to be attached to a medium to extra large size tibial trial base for accommodating the width of the femoral runner;

a ball plunger assembly, a plurality of indents, and a threaded screw, the ball plunger assembly being formed in the anterior surface of the guide block and being engagable with the indents formed in the guide means to selectively adjust the angular alignment of the guide means with respect to the lateral-medial axis perpendicular to the longitudinal axis of the tibia, the threaded screw being insertable through a guideway formed in the guide means, the threaded screw being adapted to be threaded into the guide block for tightening against the guide means to lock the guide means in position with respect to the lateral-medial axis perpendicular to the longitudinal axis of the tibia; and means for interlocking the guide block to the tibial trial base during resection; a handle having a central axis with opposed proximal and distal ends, the distal end including means for interlocking the guide block to the tibial trial base, the handle remaining fixed to the tibial trail during the resection process.

* * * * *